United States Patent [19]

Sugai et al.

[11] Patent Number: 4,472,973
[45] Date of Patent: Sep. 25, 1984

[54] ULTRASONIC FLAW DETECTING APPARATUS OF ELECTRONICALLY SCANNING TYPE

[75] Inventors: Kazuo Sugai, Kitaibaraki; Yasuaki Sato, Hitachi; Hirotoshi Kino, Hitachi; Shuichi Hiruoka, Hitachi, all of Japan

[73] Assignees: Hitachi, Ltd.; Hitachi Engineering Co., Ltd., both of Tokyo, Japan

[21] Appl. No.: 389,911

[22] Filed: Jun. 18, 1982

[30] Foreign Application Priority Data

Jun. 22, 1981 [JP] Japan .................... 56-95250

[51] Int. Cl.³ .................................. G01N 29/04
[52] U.S. Cl. ............................ 73/626; 73/628
[58] Field of Search ............ 73/619, 625, 626, 628, 73/609

[56] References Cited
U.S. PATENT DOCUMENTS

| | | | |
|---|---|---|---|
| 4,173,007 | 10/1979 | McKeighen et al. | 73/625 |
| 4,234,940 | 11/1980 | Iinuma | 73/626 |
| 4,241,610 | 12/1980 | Anderson | 73/626 |
| 4,309,906 | 1/1982 | Northeved et al. | 73/625 |
| 4,334,432 | 6/1982 | Gill | 73/625 |
| 4,348,902 | 9/1982 | Tachita et al. | 73/626 |
| 4,354,388 | 10/1982 | Diepers et al. | 73/628 |
| 4,372,323 | 2/1983 | Takemura et al. | 73/625 |

*Primary Examiner*—Anthony V. Ciarlante
*Attorney, Agent, or Firm*—Antonelli, Terry & Wands

[57] ABSTRACT

An ultrasonic flaw detecting apparatus of electronically scanning type comprises a plurality of ultrasonic vibrator elements disposed in an arcuate array, wherein groups of N vibrator elements arrayed in the circumferential direction of an object under test are sequentially changed over to one another on one-by-one base to thereby scan an object under test with ultrasonic beams. By controlling phases of pulse signals applied to the individual vibrator elements, a region of focus of the ultrasonic beams is set at a predetermined depth of the object under test. For reception, only the echoes reflected from a predetermined focal range are selectively extracted by providing corresponding window or gate means.

14 Claims, 11 Drawing Figures

ULTRASONIC FLAW DETECTING APPARATUS OF ELECTRONICALLY SCANNING TYPE

The present invention generally relates to an ultrasonic flaw detecting apparatus in which a group of ultrasonic vibrator elements disposed in an array are selectively excited through electronic switching means to scan an object under test with ultrasonic beams emitted by the excited vibrator elements. More particularly, the invention concerns an ultrasonic flaw detecting apparatus of the electronically scanning type in which the ultrasonic beams are focussed to attain sector scanning.

The ultrasonic flaw detecting apparatus of the electronically scanning type in which the ultrasonic vibrator elements disposed in an array are selectively excited through electronic switching means for scanning an object under test with the ultrasonic beams is known well in the art.

With the ultrasonic flaw detector of the electronically scanning type as mentioned above, it is possible to perform sector scanning in which the depth of focusses or focal points of the ultrasonic beams is maintained constant within the body of the object under test independent of variations in the angle of incidence of the ultrasonic beams. The ultrasonic echo signal thus obtained is to be satisfied in respect with azimuth resolution and detection sensitivity over a wide range of measurement. However, the hitherto-known ultrasonic flaw detection system suffers a shortcoming in that flaws present in sectional images of an object under test as displayed by a B-scope display system can not be discriminated from one another, because the flaws are displayed in superposition.

An object of the present invention is to provide an ultrasonic flaw detecting apparatus which is immune to the drawback of the hitherto-known apparatus as mentioned above and which is capable of evaluating flaws in an object under test with improved accuracy over a wide range.

According to an aspect of the invention, there is provided an ultrasonic flaw detecting apparatus which comprises a plurality of ultrasonic vibrator elements disposed in an arcuate array in which groups each including a predetermined number (N) of the vibrator elements are sequentially excited through electronic switch means while varying stepwise the delay times involved in excitations of the individual vibrator elements so that the vibrator elements may transmit and receive the ultrasonic beams at the respective predetermined phases, thereby allowing the object under test to be scanned with focussed ultrasonic beams to detect possible flaws. A region at which the ultrasonic beams emitted by the vibrator elements as they are excited are focussed is set at a predetermined desired depth in the object under test and an appropriate focal range gate or window is provided so that only those coming from the region of focus are selectively taken out when the echoes are received.

The above and other objects, features and advantages of the present invention will be more apparent from description of preferred embodiments thereof. The description makes reference to the accompanying drawings, in which:

FIGS. 2a and 2b to FIG. 4 are views for illustrating graphically focussed states of ultrasonic beams;

Figure 1A:
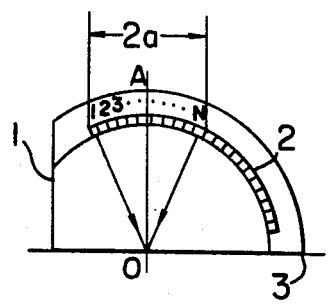
FIGS. 1a and 1b show an ultrasonic beam transmitting and receiving transducer array (probe array) in a front view and a side view, respectively.
Figure 1B:
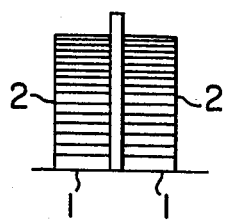

Now, the invention will be described in conjunction with preferred embodiments thereof by referring to the accompanying drawings. FIG. 1a shows in a front view a typical example of a transmitting and receiving transducer (or so-called probe array) which may be used in carrying out the invention, and FIG. 1b is a side view of the transducer. Referring to FIG. 1a, a reference numeral 1 denotes an arcuate medium having a semi-circular surface formed about a center point O, on which surface there are arrayed a group of ultrasonic vibrator elements 2 in number M. At a given transmitting and receiving angle, ultrasonic beams produced by those vibrator elements in number N which are located in a range 2a are focussed onto the center O. More specifically, when N ultrasonic vibrator elements are simultaneously excited, all the ultrasonic beams produced by these vibrator elements are focussed on the point O which is the center of curvature of the semicircle defined by vibration planes of the individual ultrasonic vibrator elements 2. Thus, a transmitting and receiving transducer can be realized which is excellently suited for detection of surface flaws.

Figure 2A:
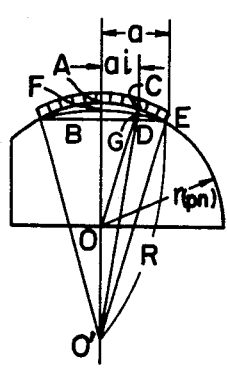
Figure 2B:
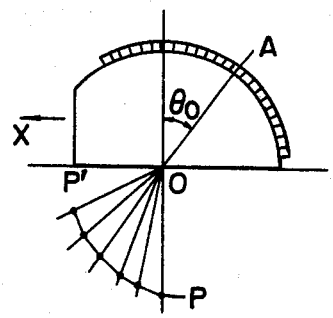

FIGS. 2a and 2b illustrate the manner in which the ultrasonic beams are focussed within the interior of an object under test. Referring to FIG. 2a, when a point at which a line CO extending from a given position C (with a distance $a_i$ from the normal line) to the center of curvature O intersects a circumferential plane EF defined about a center $O'$ with a radius R is represented by G, a distance $d'_1$ between the points G and C shown in FIG. 2a is given by the following expression:

$$d'_i = r - \sqrt{\frac{r^2(r^2 - a^2)}{r^2 - a_i^2}} - \left( R - \sqrt{\frac{R^2(R^2 - a^2)}{R^2 - a_i^2}} \right) \tag{1}$$

Accordingly, by dividing the distance $d'_i$ by the velocity of sound $v_a$, there is derived a time $t'_i$ which is required for the ultrasonic wave generated at a circumferential plane AE to reach the circumferential plane EF, the time $t'_i$ being thus expressed as follows:

$$t'_i = \frac{d'_i}{v_a} \tag{2}$$

It will thus be appreciated that the ultrasonic beams produced by the individual vibrator elements identified by 1 to N can be focussed on the point $O'$ by exciting sequentially these vibrator elements with corresponding time delays $t_1, \ldots, t_N$, respectively.

FIG. 2b is a view to illustrate the sector scanning. Referring to this figure, there is shown a path or locus which is followed by a focal point P as the center axis OA of the vibrator element group consisting of N vibrator elements is moved in a circumferential direction, i.e. when angle of incidence $\theta_o$ of the ultrasonic beam is varied. In the case of a hitherto-known ultrasonic flaw detecting system of electronically scanning type in which the sector scanning is effected by exciting the 1st to N-th vibrator elements with constant delay times $t_1$, ..., $t_N$, respectively, the path or locus followed by the focal point of the ultrasonic beam can be represented by a curve PP'. In this connection, it is to be noted that the path PP' is in an arcuate form when the velocity of sound in the medium 1 is equal to the sound velocity within the object 3 under test.

Accordingly, in the case the ultrasonic flaw detection is carried out in a composite scanning manner in which the sector scanning mentioned above is combined with linear scanning effected by displacing the transmitting-/receiving transducer constituted by ultrasonic vibrator elements in the direction X along the surface of the object under test, there coexist in the interior of the object under test both the focussed region and the defocussed region. As the consequence, there may occur the case in which desired effect due to the focussing of the ultrasonic beams does not make appearance so significantly as it is expected.

Further, it should be mentioned that the angle of incidence $\theta_o$ is determined by the distance between the adjacent vibrator elements. This is because the focussed ultrasonic beam impinges onto the object 3 under test with the center axis of the ultrasonic beam passing through the center of curvature O. For this reason, there may be produced in dependence of the set value of the incidence angle $\theta_o$ a region in which both longitudinal and transverse wave modes coexist in the interior of the object under test and/or a case in which efficiency of beam transmission and reception is lowered and/or a region within the body of the object under test in which the scanning density or rate of the ultrasonic beam is decreased. Under the circumstances, the arcuate array of the ultrasonic vibrator elements can not fully be made use of, giving rise to problems remaining to be solved.

With the invention, it is also intended to eliminate the shortcomings of the hitherto-known ultrasonic flaw detecting method as mentioned above.

Figure 3:
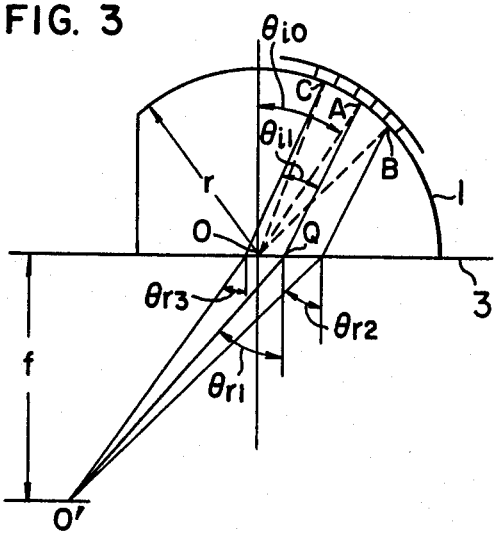
Figure 4:
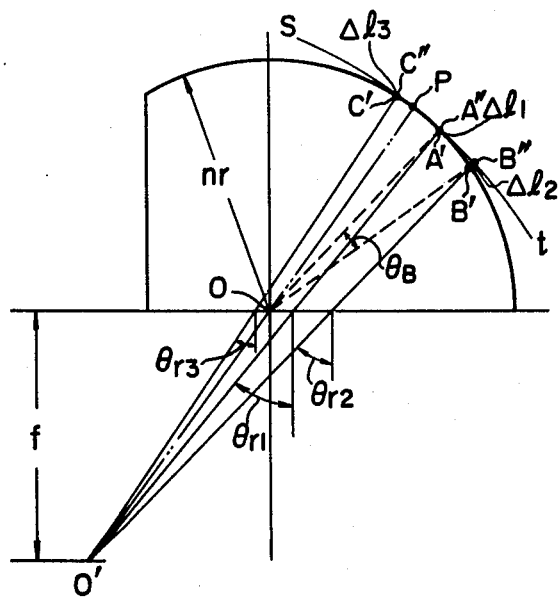

FIGS. 3 and 4 graphically illustrate the manner in which the delay times imparted to the individual vibrator elements, respectively, are determined with the aid of approximate expressions. The graphic representation shown in FIG. 3 is made on the assumption that the velocity of sound $v_1$ (m/s) in the arcuate medium 1 is different from the sound velocity $v_2$ (m/s) in the object 3 under test, as usually the case in most of practical applications of the ultrasonic flaw detection.

Referring to FIG. 3, consideration will be made on the assumption that the ultrasonic beam is focussed at a desired depth f within the body of the object 3 under test by using an array of N vibrator elements where N represents a given number and that an angle formed between the center axis of the ultrasonic beam and a line normal to the surface of the object under test is set at a desired angle of refraction $\theta_{r1}$ (e.g. at the angle at which a relatively high efficiency can be assured for the beam transmission and reception). It is assumed that the angle $\theta_{io}$ formed between a straight line AO connecting the center point A of a given vibrator element group and the center of curvature O of the acruate medium 1, on one hand, and the line normal to the surface of the object under test at the point O, on the other hand, represents the angle of incidence of the ultrasonic beam, which angle of incidence $\theta_{io}$ is determined by the geometrical disposition of the ultrasonic vibrator elements. It is also assumed that this angle of incidence $\theta_{io}$ differs from the incidence angle $\theta_{i1}$ which corresponds to the desired angle of refraction $\theta_{r1}$. Further it is required to deflect the ultrasonic beam transmitted and received at the center point A (i.e. center vibrator element) of the given vibrator element group so that the beam travels along a line segment AQ and passes through the focal point O'. Additionally, all the ultrasonic beams transmitted and received by the other vibrator elements of the given vibrator element group have to be so deflected that all the beams reach the position corresponding to the focal point O' in phase with one another. For example, the ultrasonic beams transmitted and received by the vibrator elements located a positions or points B and C disposed with a predetermined distance from the center point A have to be deflected so that the angles of refraction become equal to $\theta_{r2}$ and $\theta_{r3}$, respectively, in order thaat these beams pass through the focal point O'. In this way, all the ultrasonic beams produced by all the individual vibrator elements constituting the given group can be focussed onto the focal point O'.

In the case of a graphic representation shown in FIG. 4, the beam paths withn the arcuate medium 1 are standardized in terms of the velocity of sound $v_2$ (m/s) in the interior of the object 3 under test with a view to facilitating illustration of the travelling paths of the individual ultrasonic beams shown in FIG. 3. Accordingly, the radius of curvature of the arcuate medium 1 is represented by a product of $\eta$ and r, where $\eta$ represents a quotient obtained by dividing the velocity of sound $v_2$ in the object 3 under test by the sound velocity $v_1$ within the arcuate medium 1. Further, points A', B' and C' located on the circle having the radius of curvature $\theta.r$ correspond, respectively, to the points A, B and C of the vibrator element group shown in FIG. 3.

According, in order that all the ultrasonic beams produced by the individual vibrator elements be focussed onto a focal point located at a depth f determined by correspondingly selecting the angle of refraction $\theta_{r1}$ of the center beam, the group of the vibrator elements in number N have to be arrayed on an arc $\widehat{st}$ depicted about the focal point O' defining the center of curvature with the radius of curvature equal to the length of the line segment O'P ($=l_o$), and additionally the center of the arcuate array of the vibrator elements has to be located on the extension of the line segment O'A. On these equivalent conditions, the individual vibrator elements have to be excited for transmission and reception of the ultrasonic beams.

When the lengths of line segments O'A', O'B' and O'C' extending from the focal point O' to the points A', B' and C', respectively, in the vibrator element array disposed on the circumferential surface of the arcuate medium 1 are represented by $l_1$, $l_2$ and $l_3$, respectively, the lengths of the individual segments as well as the angles of refraction $\theta_{r2}$ and $\theta_{r3}$ can be determined mathematically as mentioned below:

$$l_o = \frac{f}{\cos\theta_{rn}} + \eta \cdot r \quad (3)$$

where $\theta_{rn}$ of the term $\cos\theta_{rn}$ is given by the following expression (4):

$$\theta_{rn} = \tan^{-1}\frac{f \cdot \tan\theta_{r1} - r(\sin\theta_{io} - \cos\theta_{io} \cdot \tan\theta_{i1})}{f} \quad (4)$$

$$l_1 = \frac{f}{\cos\theta_{r1}} + \eta \cdot \frac{r \cdot \cos\theta_{io}}{\cos\theta_{i1}} \quad (5)$$

$$l_2 = \frac{\eta \cdot r \cdot \sin\theta_{c2} + f}{\cos\theta_{r2}} \quad (6)$$

where $\theta_{c2}$ of the term $\sin\theta_{c2}$ in the above expression (6) is given by the following expression (7):

$$\theta_{c2} = \sin^{-1}\frac{l_1 \cdot \cos\theta_{r1} - f}{\eta \cdot r} - \theta_B \quad (7)$$

where $\theta_B$ represents the distance of a given one of the vibrator elements relative to the center axis of the arcuate vibrator array, and $$l_3 = \frac{\eta \cdot r \cdot \sin\theta_{cs} + f}{\cos\theta_{rs}} \quad (8)$$

where $\theta_{cs}$ is given by the following expression:

$$\theta_{cs} = \sin^{-1}\frac{l_1 \cdot \cos\theta_{r1} - f}{\eta \cdot r} + \theta_B \quad (9)$$

Further, $\theta_{r2}$ and $\theta_{r3}$ are given by the following expressions (10) and (11):

$$\theta_{r2} = \tan^{-1}\frac{\eta \cdot \cos\theta_{c2} + f \cdot \tan\theta_M - r(\sin\theta_{io} - \cos\theta_{io}\tan\theta_{i0})}{\eta \cdot r \cdot \sin_{c2} + f}$$

$$\theta_{r3} = 2\theta_{r1} - \theta_{r2} \quad (11)$$

When the lengths of line segments A'A'', B'B'' and C'C'' are represented by $\Delta l_1$, $\Delta l_2$ and $\Delta l_3$, respectively, these lengths can be determined as follows:

$$\Delta l_1 = l_o - l_1 \quad (12)$$

$$\Delta l_2 = l_o - l_2 \quad (13)$$

$$\Delta l_3 = l_o - l_3 \quad (14)$$

Accordingly, when the distances determined by the expressions (12), (13) and (14) are, respectively, divided by the velocity of sound $v_2$, there are then obtained the times $\tau_1$, $\tau_2$ and $\tau_3$ required for the ultrasonic waves produced at the arc st to reach the circumferential surface of the arcuate medium. Namely, $$\tau_1 = \frac{\Delta l_1}{v_2} \quad (15)$$

$$\tau_2 = \frac{\Delta l_2}{v_2} \quad (16)$$

$$\tau_3 = \frac{\Delta l_3}{v_2} \quad (17)$$

In this manner, the ultrasonic beams produced by the individual vibrator elements can be made convergent by performing the beam transmission and reception with time delays determined in correspondence with the 1st to the N-th vibrator elements, whereby the azimuth resolving power as well as the detection sensitivity of the ultrasonic flaw detector can be improved.

In the light of the foregoing, it will be appreciated that when the sector scanning is executed, the delay times determined, respectively, in correspondence with the 1st to the N-th vibrator elements have to be provided for each of the set angles in order to maintain the depth of the focal point to be constant.

Further, when the delay times provided for the excitation for the individual vibrator elements, respectively, are controlled in accordance with the theoretical expressions mentioned above, it is possible to set n varieties of the depths of focal points in the direction depthwise of the object under test. Thus, by automatically and successively changing over the set depth of focus from a small to a great magnitude, the azimuth resolution and the detection sensitivity of the ultrasonic flaw detector can be improved over the whole depth thicknesswise of the object under test.

Figure 5:
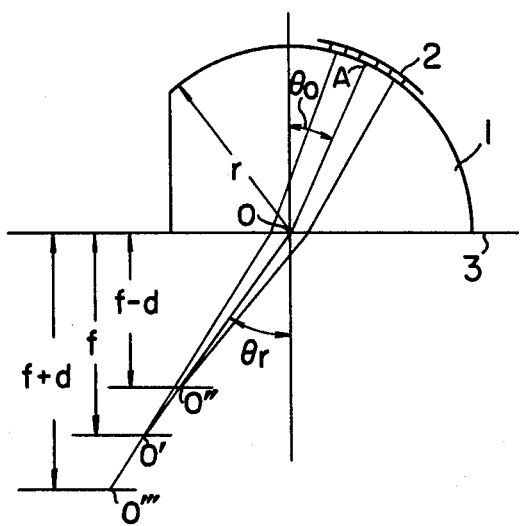
FIG. 5 is a view to illustrate a focal range gate or window made use of in carrying out the invention.

Next, reference is made to FIG. 5. Within tolerance ranges (f−d) and (f+d) of the desired depth of focus f of the center beam AO incident on the object 3 under test at the angle of incidence $\theta_o$, propagation times $t_1$ and $t_2$ required for the center beam to travel along the paths AOO'' and AOO''', respectively, can be determined from the following expressions:

$$t_1 = \frac{2r}{v_1} + \frac{2(f-d)}{v_2\cos\theta_r} \quad (18)$$

$$t_2 = \frac{2r}{v_1} + \frac{2(f+d)}{v_2\cos\theta_r} \quad (19)$$

In this connection, it is proposed according to another aspect of the invention that a focal range gate or window function is provided which enables a derivation from the ultrasonic beam of which focus is controlled to lie at the desired depth f within the object under test, of only those ultrasonic echo signals which are reflected at the ranges of regions (f−d) and (f+d) where the azimuth resolution as well as the detection sensitivity of the ultrasonic flaw detector is relatively improved as mentioned above. Such a focal range gate or window function can be realized by imparting the propagation times difference $(t_2 - t_1)$ of the center ultrasonic beam determined from the above expressions (18) and (19) to the ultrasonic echoes as received, whereby only the echo signal reflected at the focal depth regions or focal ranges (f−d) and (f+d) located adjacent to the focal point of the center beam can be taken out for evaluation. In the foregoing, the focussing of the ultrasonic beams by controlling correspondingly the delay times for the 1st to the N-th vibrator elements, respectively, and the realization of the focal range gate or window function by making use of the propagation time difference of the center beam have been theoretically discussed. In the following, description will be made on an exemplary embodiment of the ultrasonic flaw detecting apparatus according to the invention embodied on the basis of the theoretical analyses described above.

Figure 6:
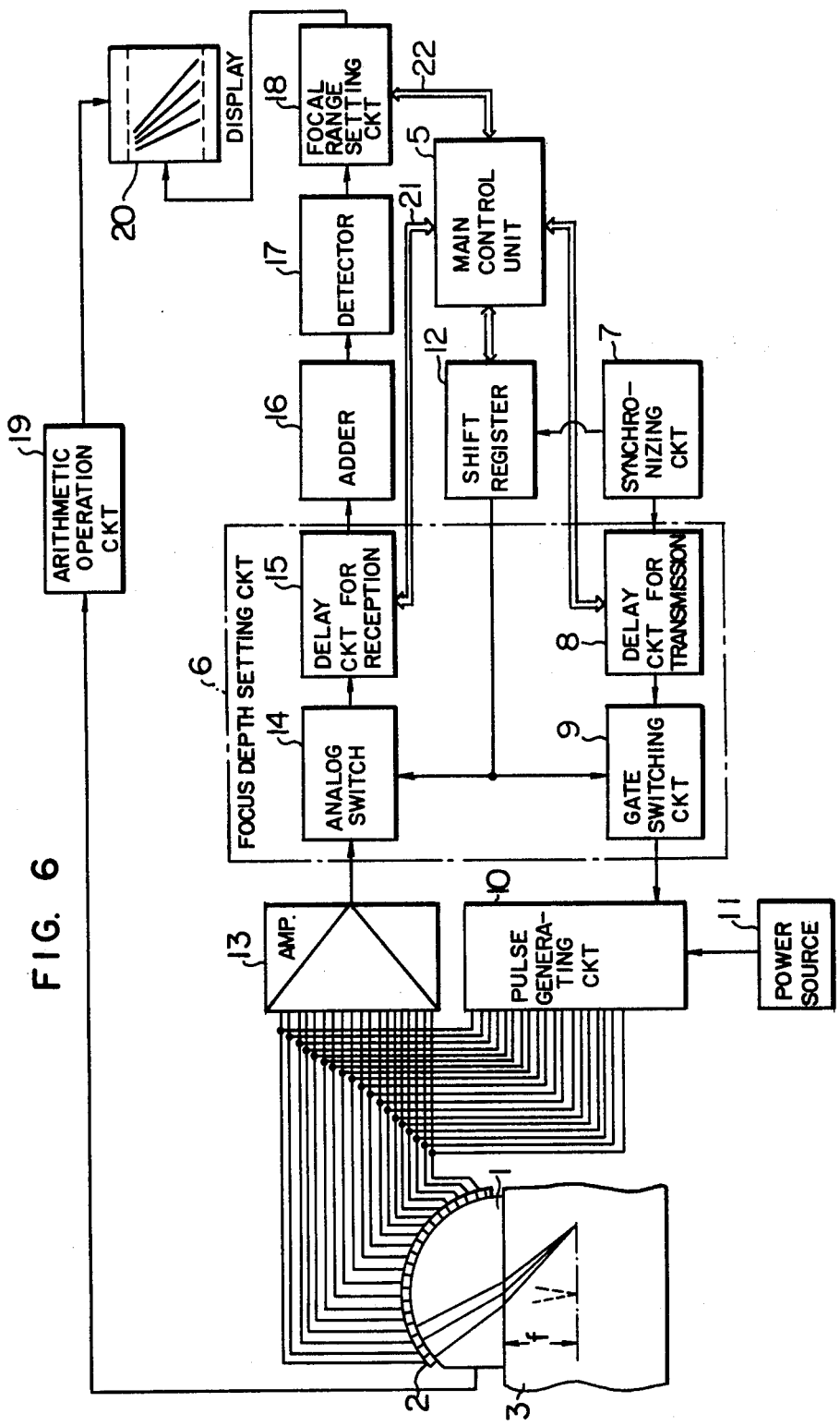
FIG. 6 is a block diagram showing a general arrangement of an ultrasonic flaw detecting apparatus according to an embodiment of the invention.
Figure 7:
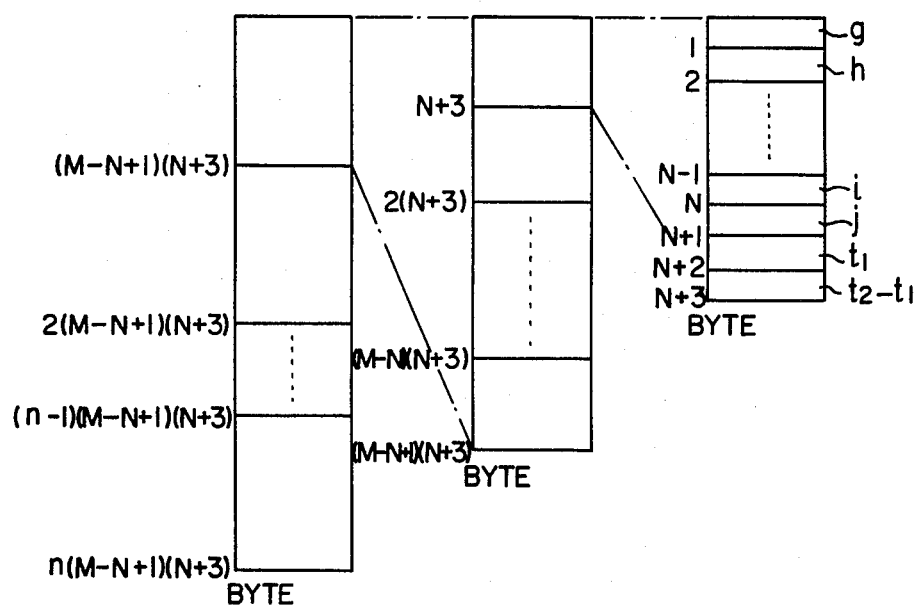
FIG. 7 is a chart illustrating a table structure of a read-only memory (ROM)

Referring to FIG. 6 which shows a circuit arrangement of an ultrasonic flaw detector according to the invention, a reference numeral 5 denotes a main control unit which incorporates therein a microcomputer and a read-only memory or ROM for storing various data required for the controls. To this end, a data table shown in FIG. 7 is stored in the ROM and so prepared that the desired focal depths (i.e. depths of focus) in an object to be tested or examined can be definitely determined and that only the echo signals reflected from the desired focal depth range or region defined hereinbefore can be extracted. More specifically, the table contains a data group comprising excitation delay data 1 to N defining, for the individual vibrator elements, the respective delay times corresponding to the set angle of incidence i of the center beam produced by the center vibrator element in the array of N elements, data for the time point $t_1$ at which the focal range gate or window period is initiated, and data for the focal range gate or window period $(t_2-t_1)$. The table thus prepared and having $(N+3)$ bytes is stored in the ROM. Further, for controlling the focussing of the ultrasonic beams so as to be located at the predetermined depth f in the course of the electronic scanning operation in which the group of N vibrator elements among M elements in total are sequentially shifted from one to another on the single element base, the excitation delay data $(g-i)$ for the respective vibrator elements and the focal range window setting data $(t_1; t_2-t_1)$ are stored in a memory area or table of $(M-N+1)(N+3)$ bytes. Additionally, data for automatically and exchangeably controlling n different depths f of focus preset stepwise for allowing the flaw detection to be performed over the whole depth of an object under test is also stored in a similarly prepared table in a memory area of the ROM having $n(M-N+1)(N+3)$ bytes.

Turning to FIG. 6, when an address designating signal is issued from the main control unit 5, delay time data corresponding to the addressing signal is supplied to a focus depth setting circuit 6 by way of a control bus 21. The focus depth setting circuit 6 is composed of a delay circuit 8 for transmission, a delay circuit 15 for reception, a gate switching circuit 9 and an analog switch 14. A synchronizing circuit 7 produces a trigger signal which is supplied to the delay circuit 8 for transmission which may be constituted by a variable delay line having an adjustable tap. Additionally, the delay circuit 8 is further supplied with the desired excitation delay data signal from the delay data storage constituted by the ROM as described hereinbefore, whereby the respective trigger signals are delayed by times corresponding to the respective N ultrasonic transmitter or vibrator elements and subsequently supplied to a pulse generator circuit 10 through the gate switching circuit 9. The pulse generator circuit 10 then applies pulse voltages to the group of the ultrasonic vibrator elements for excitation thereof. A reference numeral 11 denotes a power supply source for the pulse generating circuit 10. The trigger signal produced by the synchronizing circuit 7 is also applied to a shift register 12 which serves to shift one-by-one N vibrator elements to be excited in response to each trigger signal input, to thereby allow the sector scanning to be effected with the focussed ultrasonic beam at the variable angle of incidence j, while constantly maintaining the focus depth f to be constant.

The echo signals received by the ultrasonic receiving elements 2 which correspond to the N ultrasonic transmitting elements and having different phases are supplied to the analog switch 14 after having been amplified by an amplifier 13. It should be noted that the ultrasonic wave transmitting channel and the ultrasonic echo receiving channel are synchronized with each other by means of the synchronizing circuit 7 and the shift register 12. The ultrasonic echo signal is supplied to the delay circuit 15 for reception from the analog switch 14. The delay circuit 15 is additionally supplied with delay time data equivalent to those supplied to the delay circuit 8 for transmission from the delay data storage, whereby the ultrasonic echo signals or different phases are caused to coincide in time with the echo signal corresponding to the center beam for each of the set angles of incidence j. The output signals from the delay circuit 15 are supplied to an adder 16 to restore the signal of the original waveform, which is then detected by a detector 17.

Next, operation of the focus range gate circuit 18 will be described by referring to waveform diagrams shown in FIG. 8. The main control unit 5 produces a focal range gate position setting signal 802 corresponding to each of the set angles of incidence j, which signal 802 is supplied to the focal range setting circuit 18 through a control bus 22. In response to the application of the focal range gate position setting signal, two counters incorporated in the focal range setting circuit 18 and connected in cascade are activated and deactivated by data signals representative of the beginning $t_1$ of the focal range gate or window and the period $(t_2-t_1)$ thereof, respectively, whereby only the echo signals received from the locations lying in the vicinity of the desired focal point (O', FIG. 5) are extracted from the received echo signals 801. The extracted echo signals or video signal 803 is supplied to a sectioned image display circuit 20 together with position data signals which represents the vibrator elements are excited and obtained from an arithmetic operation circuit 19.

Figure 8:
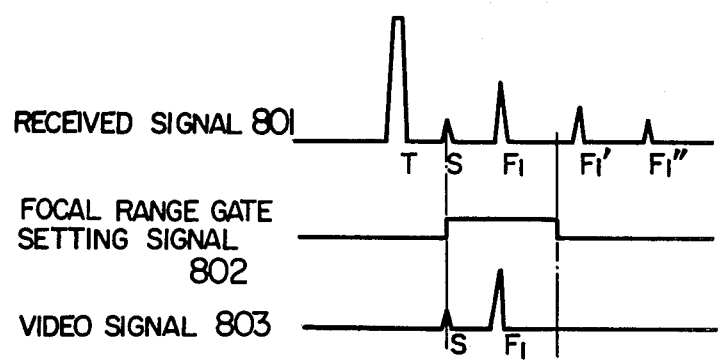
FIG. 8 is a time chart for illustrating the setting of a focal range gate or window.
Figure 9:
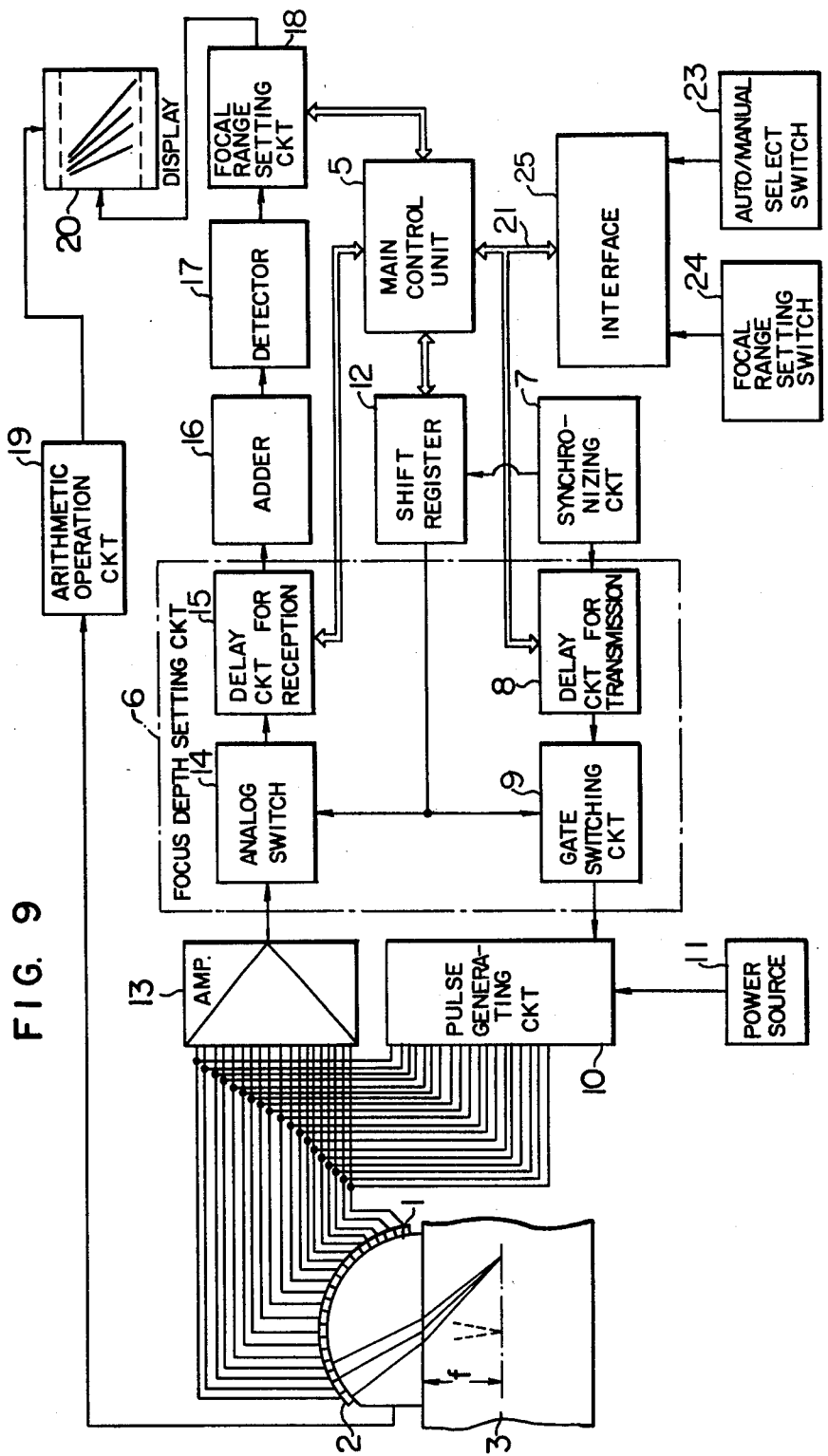
FIG. 9 is a block diagram showing a general arrangement of the ultrasonic flaw detecting apparatus according to another embodiment of the invention.

In the case of the embodiment shown in FIG. 8, the desired focal range is set in the vicinity of the predetermined depth of focus f, whereby only the echo signals reflected from the focal range are extracted. In contrast, FIG. 9 shows a version in which the control bus 21 of the main control unit 5 is imparted with an interface function such as PIA (peripheral interface, for example), so that series of the focus depth setting data and the focal range gate or window setting data stored in the ROM may be outputted from the main control unit 5 in response to external command signal supplied through an "automatic" and "manual" mode change-over switch 23.

When the switch 23 is set to the mode "automatic", the data of concern are automatically successively supplied to the focus depth setting circuit 6 and the focal range gate or window setting circuit 18 from the ROM of the aforementioned arrangement through the control bus 21 extending between the interface 25 and the main control unit 5, to thereby perform the sector scanning with the focal range gate or window being varied.

On the other hand, when the switch 23 is set to the "manual" mode, similar sector scanning can be performed by selecting given data from those stored in the ROM of the main control unit 5.

Further, in the case of the flaw detecting sector scanning in which the focus depth is automatically varied stepwise over the whole depth of the object under test, the focus range gates or windows corresponding to the respective focus depths can be partially superposed on one another, to thereby prevent the flaw representing echo from being undetected.

A focal range window position selecting switch 24 which is capable of bit transformation may be additionally provided for the interface 25. In that case, an external command can be supplied to the main control unit 5 through the interface 25 by appropriate manipulation of the switch 24 to effect a modified sector scanning in which a desired number of the focus depths are carried out from all the focus depths set stepwise throughout the whole depth of the object under test and stored in the ROM.

What is claimed is:

1. An ultrasonic flaw detecting apparatus of electronically scanning type, comprising:

a probe array having a plurality of ultrasonic vibrator elements for transmitting ultrasonic beams to an object under test and for receiving echoes from said object, said vibrator elements being arranged on a medium wherein velocities of propagation of said ultrasonic beams in said medium and in said object are different and said ultrasonic beams and received echoes pass through said medium;

means for deflecting and scanning said ultrasonic beams in said object by sequentially switching each of groups of said ultrasonic vibrator elements;

means for sequentially exciting each of said vibrator elements to transmit said ultrasonic beams to said object by applying relative different delay times to timings of the excitation of said vibrator elements;

means for detecting a flaw possibly present in a body of said object by utilizing said received echoes;

means for controlling said delay times to focus said ultrasonic beams transmitted by all of said vibrator elements in any one of said groups on a predetermined region within said object;

means for controlling said delay times to move said focussed ultrasonic beams in a horizontal direction while maintaining a predetermined depth of focus of said ultrasonic beams within said object; and means for controlling said delay times to displace said depth of focus of said ultrasonic beams in a vertical direction within said object.

2. An ultrasonic flaw detecting apparatus according to claim 1, further comprising phase adjusting means for adjusting phases between said transmitted ultrasonic beams and said received echoes by applying the same delay times to said timings of the excitation of said vibrator elements and the timings of the receipt of said echoes, and focus range gate setting means for setting data of timings for extracting said echoes and a focal range gate period for each of different depth of focus regions.

3. An ultrasonic flaw detecting apparatus according to claim 2, wherein said focal range gate periods are partially superposed on one another.

4. An ultrasonic flaw detecting apparatus according to claim 3, further comprising a read-only memory for storing said data of timings of extracting said echoes and focal range gate periods, and data of said delay times.

5. An ultrasonic flaw detecting apparatus according to claim 4, wherein said probe array is an arcuate array having said plurality of ultrasonic vibrator elements disposed on at least a semi-circular surface portion of said medium, said medium being an arcuate medium.

6. An ultrasonic flaw detecting apparatus according to claim 3, wherein said probe array is an arcuate array having said plurality of ultrasonic vibrator elements disposed on at least a semi-circular surface portion of said medium, said medium being an arcuate medium.

7. An ultrasonic flaw detecting apparatus according to claim 1, further comprising a read-only memory for storing date of said delay times.

8. An ultrasonic flaw detecting apparatus according to claim 7, wherein said probe array is an arcuate array having said plurality of ultrasonic vibrator elements disposed on at least a semi-circular surface portion of said medium, said medium being an arcuate medium.

9. An ultrasonic flaw detecting apparatus according to claim 1, wherein said probe array is an arcuate array having said plurality of ultrasonic vibrator elements disposed on at least a semi-circular surface portion of said medium, said medium being an arcuate medium.

10. An ultrasonic flaw detecting apparatus according to claim 2, further comprising a read-only memory for storing data of said delay times.

11. An ultrasonic flaw detecting apparatus according to claim 10, wherein said probe array is an arcuate array having said plurality of ultrasonic vibrator elements disposed on at least a semi-circular surface portion of said medium, said medium being an arcuate medium.

12. An ultrasonic flaw detecting apparatus according to claim 2, further comprising a read-only memory storing said data of timings of extracting said echoes and focal range gate periods, and data of said delay times.

13. An ultrasonic flaw detecting apparatus according to claim 12, wherein said probe array is an arcuate array having said plurality of ultrasonic vibrator elements disposed on at least a semi-circular surface portion of said medium, said medium being an arcuate medium.

14. An ultrasonic flaw detecting apparatus according to claim 2, wherein said probe array is an arcuate array having said plurality of ultrasonic vibrator elements disposed on at least a semi-circular surface portion of said medium, said medium being an arcuate medium.

* * * * *